United States Patent
Profizi et al.

(10) Patent No.: US 11,680,024 B2
(45) Date of Patent: Jun. 20, 2023

(54) **USE OF *PENICILLIUM BRASILIANUM* FOR STIMULATING PLANT GROWTH**

(71) Applicant: Etablissements J. SOUFFLET, Nogent sur Seine (FR)

(72) Inventors: Camille Simone Madeleine Profizi, Nantes (FR); Sébastien Michel Edouard Ptas, Nogent sur Seine (FR)

(73) Assignee: Etablissements J. SOUFFLET, Nogent sur Seine (FR)

( * ) Notice: Subject to any disclaimer, the term of this patent is extended or adjusted under 35 U.S.C. 154(b) by 1036 days.

(21) Appl. No.: 16/462,906

(22) PCT Filed: Nov. 28, 2017

(86) PCT No.: PCT/EP2017/080725
§ 371 (c)(1),
(2) Date: May 21, 2019

(87) PCT Pub. No.: WO2018/096183
PCT Pub. Date: May 31, 2018

(65) Prior Publication Data
US 2020/0085067 A1  Mar. 19, 2020

(30) Foreign Application Priority Data

Nov. 28, 2016 (EP) .................... 16306568

(51) Int. Cl.
| | | |
|---|---|---|
| *A01N 63/36* | (2020.01) | |
| *A01C 21/00* | (2006.01) | |
| *C05F 11/08* | (2006.01) | |
| *C05B 1/00* | (2006.01) | |
| *C12N 1/14* | (2006.01) | |
| *C12R 1/80* | (2006.01) | |

(52) U.S. Cl.
CPC .............. *C05F 11/08* (2013.01); *A01C 21/00* (2013.01); *A01N 63/36* (2020.01); *C05B 1/00* (2013.01); *C12N 1/145* (2021.05); *C12R 2001/80* (2021.05)

(58) Field of Classification Search
None
See application file for complete search history.

(56) References Cited

FOREIGN PATENT DOCUMENTS

| FR | 2243257 | A1 | 4/1975 |
|---|---|---|---|
| FR | 2694284 | A1 | 2/1994 |
| WO | 2015130911 | A1 | 9/2015 |
| WO | 2015180624 | A1 | 12/2015 |
| WO | 2016030472 | A1 | 3/2016 |

OTHER PUBLICATIONS

Schurmann et al.(Austin, dehydroaustin and other metabolites from Penicillium brasilianum (Quimica Nova (2010), 33(5), 1044-1046) (Year: 2010).*
Panagiotou et al.( Penicillium brasilianum as an enzyme factory; the essential role of feruloyl esterases for the hydrolysis of the plant cell wall(Journal of Biotechnology (2007), 130(3), 219-228) (Year: 2007).*
Panagiotou et al.( Production and partial characterization of arabinoxylan-degrading enzymes by Penicillium brasilianum under solid-state fermentation, Applied Microbiology and Biotechnology (2006), 72(6), 1117-1124) (Year: 2006).*
Jorgensen et al.( Investigation of cellulase and hemicellulose production in Penicillium brasilianum using capillary electrophoresis, Abstracts of Papers, 223rd ACS National Meeting, Orlando, FL, United States, Apr. 7-11, 2002 (2002) (Year: 2002).*
Mothapo, Nape V. et al., "Nitrous Oxide Producing Activity of Diverse Fungi from Distinct Agroecosystems," Soil Biology & Biochemistry, vol. 66, Jan. 1, 2013, pp. 94-101.
Thygesen, A. et. al., "Production of Cellulose and Hemicellulose-Degrading Enzymes by Filamentous Fungi Cultivated on Wet-Oxidised Wheat Straw," Enzyme and Microbial Technology, vol. 32, No. 5, Apr. 8, 2003, pp. 606-615.
PCT International Search Report for Application No. PCT/EP2017/080725, dated Feb. 28, 2018, 6 pp.

* cited by examiner

*Primary Examiner* — Alton N Pryor
(74) *Attorney, Agent, or Firm* — Soquel Group LLC

(57) ABSTRACT

The present invention concerns the use of an inoculum of at least one strain of *Penicillium brasilianum* for improving plant growth conditions. It also concerns a method of increasing the availability of phosphorus and/or micronutrients for plant uptake from a plant growth substrate, said method comprising applying to the plant growth substrate an effective amount of an inoculum of *Penicillium brasilianum*.

8 Claims, 4 Drawing Sheets

USE OF *PENICILLIUM BRASILIANUM* FOR STIMULATING PLANT GROWTH

CROSS-REFERENCE TO RELATED APPLICATIONS

This application claims benefit under 35 USC § 371 of PCT Application No. PCT/EP2017/080725 entitled USE OF *Penicillium brasilianum* FOR STIMULATING PLAN GROWTH, filed on Nov. 28, 2017 by inventors Camille Simone Madeleine and Sébastien Michel Edouard Pras. PCT Application No. PCT/EP2017/080725 claims priority of European Patent Application No. 16 306 568.3, filed on Nov. 28, 2016.

FIELD OF THE INVENTION

The present invention concerns microorganisms for stimulating plant growth, in particular through soil phosphorous solubilization.

BACKGROUND OF THE INVENTION

Phosphorus is a mineral which is essential to plants life. Plants meet the majority of their phosphorus needs by absorbing soluble ortho-phosphate ($HPO_4^{2-}$, $H_2PO_4^-$) from the soil solution.

However, although phosphorus is generally abundant in soils in organic and inorganic forms, it is rarely present in a form which can be directly taken up by plants. Indeed, while the only form which is usable by plants is soluble phosphorus, only 0.1% of the total phosphorus exists in such a soluble form available for plant uptake. Therefore, most of the soil phosphorus is unavailable to the plant, the majority of soil phosphorus being found either adsorbed to soil surfaces, as insoluble minerals or within insoluble organic complexes.

Phosphorus can be provided by phosphate chemical fertilizers application. However, following application, phosphate fertilizers are rapidly converted to products of lower solubility. In one growing season, it has for example been estimated that only 10-30% of the fertilizer applied was used by plants, the remainder being immobilized within the soil and therefore not being available for the plant. Additionally, repeated application of phosphorus fertilizers to agricultural soils has led to the accumulation of large phosphorus reserves within arable soils. It also triggers a eutrophication phenomenon in water bodies. Furthermore, reserves of minable phosphorus for fertilizers manufacture are dramatically decreasing. Finally, phosphate fertilizers are expensive and account for a large proportion of farm expenditure in developed countries.

Improving plants phosphorus uptake capacity is thus a priority.

One strategy to improve plants phosphorus uptake capacity is to apply microorganisms which increase the amount of soil phosphorus available to be taken up by plants.

The application of microorganisms as seed or soil treatments to increase plant phosphorus uptake has received considerable attention for a number of years. However, despite the large amount of work that has gone into the study of phosphorus solubilizing microorganisms, there have been very few developments that have led to commercially available phosphorus solubilizing inoculants that have a consistent plant growth response in soils of varying properties.

One of such phosphorus solubilizing microorganisms is the *Penicillium biliae* PB-50 strain, commercialized under the name JumpStart®. However, as underlined in Simon Anstis' thesis "*Penicillium radicum*: studies on the mechanisms of growth promotion in wheat" (2004), it was shown that in field trials and glasshouse trials, the effects of *P. biliae* PB-50 were low and/or inconsistent.

There is thus still an important need of new phosphate solubilizing microorganisms which can be used to improve plants phosphorus uptake capacity.

The solubilization of insoluble phosphorus compounds by microorganisms is generally thought to occur by either direct acidification or action of low molecular weight organic cations. Accordingly, a conventional test to assay the relative efficiency of a phosphate-solubilizing microorganism is based on the lowering of pH, owing to production of organic acids into the surrounding medium. Other conventional tests directly determine the capacity of microorganisms to solubilize tri-calcium phosphates in a specific NBRIP medium (National Botanical Research Institute's phosphate growth medium).

One known microorganism shown to solubilize phosphate in vitro is *Penicillium radicum* sp. nov. CBS100489, isolated from the rhizosphere of Australian wheat (Hocking et al. (1998) *Mycol. Res.* 102:801-806 and Whitelaw et al. (1999) *Soil Biology Biochem.* 31:655-665). Another known microorganism known to solubilize phosphate is *Penicillium expansum*, as confirmed by Panchal et al. (2015) *Eco. Env. & Cons.* 21:S259-S267. Another microorganism disclosed as increasing the growth of a plant part is *Penicillium spinulosum* (WO 2015/130911).

SUMMARY OF THE DESCRIPTION

The present inventors surprisingly identified, among 290 isolated fungus strains, one specific *Penicillium* species, namely *Penicillium brasilianum*, which was able to solubilize tri-calcium phosphates with at least the same efficiency as the known *Penicillium radicum* and *Penicillium expansum* mentioned above.

To the best of the inventors' knowledge, the capacity of this species to be used as bioterfilizer by solubilizing phosphorus was unknown until now.

The present invention thus concerns the use of an inoculum of at least one strain of *Penicillium brasilianum* for improving plant growth conditions.

Another object of the invention concerns a method of enhancing plant growth, said method comprising applying an effective amount of an inoculum of at least one strain of *Penicillium brasilianum* to the plant growth substrate and/or in or on the plant to be grown.

The present invention also relates to a method of increasing the availability of phosphorus and/or micronutrients for plant uptake from a plant growth substrate, said method comprising applying to the plant growth substrate and/or in or on a plant to be grown, an effective amount of an inoculum of *Penicillium brasilianum*.

A further object of the invention concerns a method for increasing the phosphorus uptake of a plant and/or increasing the foliar or roots biomass and/or increasing the yield (such as increasing the foliar, roots, fruits and/or grains biomass, and/or increasing leaves, roots, vegetables, fruits and/or grains number) of a plant, said method comprising applying an effective amount of an inoculum of at least one strain of *Penicillium brasilianum* to the plant growth substrate in which the plant is grown and/or in or on the plant which is grown.

The invention also concerns a composition comprising an inoculum of at least one strain of *Penicillium brasilianum* and a plant growth substrate-compatible carrier.

It further relates to the use of a composition comprising an inoculum of at least one strain of *Penicillium brasilianum* for coating plant seeds.

Another object of the invention concerns a plant seed having a coating comprising an inoculum of at least one strain of *Penicillium brasilianum*.

DETAILED DESCRIPTION

Plants

The methods of the invention are potentially useful for improving growth conditions for any type of plant.

In a particular embodiment, the plant is a crop plant. The plant may further be a turf or ornamental plant. In particular, the plant may be a monocotyledon or a dicotyledon. Preferably, the plant is a monocotyledon.

In a particular embodiment, the plant is selected from the group consisting of Gramineae plants, in particular cereals, pulses, Brassicaceae, fruit plants, vegetable plants and tuberous plants.

In a particular embodiment, said plant is a Gramineae, in particular a cereal, such as wheat, corn, rice, oat, rye, barley, ray-grass, turf grass species, or species belonging to the Genus *Lolium, Festuca, Poa, Agrostis, Trifolium, Medicago, Cynodon, Deschampsia, Zoysia, Dichondra, Phleum, Paspalum, Alopecurus, Bromus, Holcus, Elytrigia* or *Cynosurus*. In a preferred embodiment, said plant is wheat or ray-grass.

In another embodiment, said plant is a pulse such as soya, groundnut, bean, pea, lentil, chickpea, broad bean, lucerne, grass-clover, lupin and liquorice.

In another embodiment, said plant is a Brassicaceae such as rape, horseradish or mustard.

In another particular embodiment, said plant is a fruit vegetable or tuberous plant, such as lettuce, endive, cabbage, Brussel sprout, beet, parsnip, turnip, cauliflower, broccoli, radish, spinach, onion, garlic, eggplant, pepper, celery, carrot, squash, pumpkin, zucchini, cucumber, melon, strawberry, grape, raspberry, pineapple or tomato.

In the context of the invention, the plants are cultivated on a plant growth substrate.

By "plant growth substrate" is meant herein any substrate conventionally used for cultivating plants and enabling the plant growth. Such substrates are well-known from the skilled person and include the soil, mold, compost, peat, artificial soil and substrates suitable for hydroculture, in particular suitable for hydroponics, such as inorganic or organic hydroponic solution including expanded clay aggregate, growstones, coir peat, rice husks, perlite, vermiculite, pumice, sand, gravel, wood fibre, sheep wool, rock wool, brick shards or polystyrene packing peanuts.

In a particular embodiment, the plant growth substrate is the soil.

Inoculum of *Penicillium brasilianum*

As used herein, the term "inoculum" refers to any form of fungus cells, mycelium or spores, which is capable of propagating on or in a plant growth substrate, on or in the plant seeds, and/or on or in the plant when the conditions of temperature, moisture, etc, are favorable for fungal growth.

The present inventors surprisingly identified, among 290 isolated fungus strains, one specific *Penicillium* species, namely *Penicillium brasilianum*, which was able to solubilize tri-calcium phosphates with at least the same efficiency than the known *Penicillium radicum* mentioned above.

In the context of the invention, the term "*Penicillium brasilianum*" refers to a fungus species of the genus *Penicillium*, also called *Penicillium paraherquei* or *Penicillium ochrochloron* var. *paraherquei*. The type strains of this species include the strains ATCC 12072, CBS 253.55, FRR 3466 and QM 6947.

The present inventors more particularly isolated from wheat dead plant tissue from Bresse in France and wheat plant surface from Bourgogne in France and identified three new *Penicillium brasilianum* strains, which are capable to solubilize phosphate at least as efficiently as *Penicillium radicum*.

These strains are the *Penicillium brasilianum* strain O64 (also called SCCO64) deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54519, the *Penicillium brasilianum* strain O65 (also called SCCO65) deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54520 and the *Penicillium brasilianum* strain O849 deposited under the Budapest Treaty with the Centralbureau voor Schimmelcultures (CBS, Uppsalalaan 8, 3584 CT Utrecht, Netherlands) on 27 Oct. 2016 under Accession number CBS 141988.

Accordingly, in a particular embodiment, said inoculum of *Penicillium brasilianum* is an inoculum of strain(s) selected from the group consisting of *Penicillium brasilianum* strain O64, *Penicillium brasilianum* strain O65, *Penicillium brasilianum* strain O849, variants thereof and mixtures thereof. In a more preferred embodiment, said inoculum of *Penicillium brasilianum* is an inoculum of strain(s) selected from the group consisting of *Penicillium brasilianum* strain O64, *Penicillium brasilianum* strain O65, *Penicillium brasilianum* strain O849 and mixtures thereof. In a more preferred embodiment, said inoculum of *Penicillium brasilianum* is an inoculum of strain(s) selected from the group consisting of *Penicillium brasilianum* strain O64, *Penicillium brasilianum* strain O65 and mixtures thereof. In still a more preferred embodiment, said inoculum of *Penicillium brasilianum* is an inoculum of strain(s) selected from the group consisting of *Penicillium brasilianum* strain O64, *Penicillium brasilianum* strain O849 and mixtures thereof. In still a more preferred embodiment, said inoculum of *Penicillium brasilianum* is an inoculum of strain(s) selected from the group consisting of *Penicillium brasilianum* strain O65, *Penicillium brasilianum* strain O849 and mixtures thereof.

As intended herein, the term "variant" refers to:
a natural variant of a strain of the invention, i.e. a strain spontaneously obtained from a strain of the invention after incubation in a selection medium (a natural variant is thus obtained without any genetic engineering from the operator but only by natural mutation of the strain and selection of the mutated strain in a suitable medium), or
a variant of a strain of the invention comprising at least one mutation in its genome, said mutation being induced by genetic engineering, for example by directed mutagenesis or random mutagenesis, or by gene editing methods.

By "mutation" is meant herein the addition, deletion or substitution of least one nucleotide in the genome of the strain of the invention.

In all cases, the variants of the invention are from the same species as the strain from which they are derived (i.e. are identified as belonging to the *Penicillium brasilianum* species), and are capable to solubilize phosphate, in the conditions described in the Example. In particular, when inoculated in liquid NBRIP medium (National Botanical Research Institute's phosphate medium comprising glucose (10 g/l), tricalcium phosphate $Ca_3PO_4$ (5 g/l), $MgCl_2$ (5 g/l), $MgSO_4$ (2.5 g/l), KCl (0.2 g/l), $(NH_4)_2SO_4$ (0.1 g/l), pH 7) further comprising a pH indicator such as Bromophenol Blue (typically at 0.025 g/l), preferably at $1\times10^6$ spores/ml, the variant secretes, after 6 days of incubation, an amount of organic acids which enables decreasing the pH of the medium supernatant, at least at the same level, or at a lower level, than the pH obtained in the same conditions with the reference strain or with the *Penicillium radicum* sp. nov. CBS 100489 strain disclosed in Hocking et al. (1998) *Mycol. Res.* 102:801-806 and Whitelaw et al. (1999) *Soil Biology Biochem.* 31:655-66. Typically, the variant secretes under these conditions an amount of organic acids which enables decreasing the $OD_{600\ nm}$ of the medium supernatant to a level of less than 1.8, more preferably of less than 1.7, less than 1.6, less than 1.5, less than 1.4, less than 1.3, less than 1.2, less than 1.1, less than 1, less than 0.9, less than 0.5, less than 0.2 or less than 0.1, compared to a non-inoculated medium where the $OD_{600\ nm}$ is typically of about 2.4. Alternatively, the variant secretes under these conditions an amount of organic acids which enables decreasing the final pH of the medium supernatant to a level of less than 5, more preferably of less than 4.5, less than 4.4, less than 4.3, less than 4.2, less than 4, less than 3.5, less than 3, less than 2.5 or less than 2.4 compared to a non-inoculated medium where the final pH is typically of 6.3.

Any suitable method known to the skilled person can be used to cultivate the fungi used in the context of the invention. By way of example, the fungi may be cultured on a suitable growth medium, such as potato dextrose agar, for example for 7 to 14 days at 25° C. These culture methods can be used in the preparation of an inoculum for coating seeds and/or application to a field.

The fungi may also be routinely propagated on a suitable carbon source such as autoclaved moist ground wheat straw for example with added glucose, or bran. Propagation normally takes place for a period of approximately one week or more before the inoculum is ready to use. The resulting fungus propagated on a solid support may be used as such for application to the plant growth substrate and/or to the plant, preferably at root level, but may alternatively be coated onto seeds.

Still alternatively, a liquid culture of the fungus may be prepared using a conventional nutrient solution and then used as such or dried and applied to the plant growth substrate and/or to the plant, with or without a suitable carrier and/or nutrient source.

The fungal culture and/or spores may be stored using any suitable means known in the art. For example, for longer term storage, cultured fungi may be lyophilized or alternatively stored frozen in an appropriate solution, such as glycerol solution.

Composition

An object of the invention is a composition comprising an inoculum of at least one strain of *Penicillium brasilianum*, as defined in the section "Inoculum of *Penicillium brasilianum*" above and a plant growth substrate-compatible carrier.

In a particular embodiment, the composition of the invention comprises an inoculum of a mixture of the *Penicillium brasilianum* strains O64 and O65, a mixture of the *Penicillium brasilianum* strains O64 and O849, a mixture of the *Penicillium brasilianum* strains O65 and O849 or a mixture of the *Penicillium brasilianum* strains O64, O65 and O849.

As used herein, the term "plant growth substrate-compatible carrier" means any material which can be added to the plant growth substrate, as defined in the section "Plant" above without having a significant adverse effect on plant growth, substrate structure, substrate drainage or the like. In a particular embodiment, the plant growth substrate-compatible carrier is a soil-compatible carrier. Suitable plant growth substrate compatible carriers include wheat chaff, bran, ground wheat straw, peat-based powders or granules, gypsum-based granules and clays but also water or fungal growth media.

The composition may be in the form of a liquid, a slurry, a solid, a wettable powder or a dry powder.

In a particular embodiment, said composition is in the form of a seed coating. Compositions in liquid, slurry or power form can be suitable for coating seeds. When used to coat seeds, the composition may be applied to the seeds and allowed to dry. In embodiments wherein the composition is a powder, for example a wettable powder, a liquid, such as water, may need to be added to the powder before application to a seed.

The compositions of the invention may comprise one or more optional ingredients, such as one or more phosphorus sources, one or more biologically active ingredients, micronutrients, biostimulants, preservatives, polymers, wetting agents, surfactants or combinations thereof.

In a particular embodiment, the composition of the invention further comprises one or more phosphorous source.

In the context of the invention, the term "source" of a particular element is intended to mean a compound of that element which, at least in the plant growth substrate conditions under consideration, does not make the element fully available for plant uptake.

In one embodiment, the phosphorus source is rock phosphate. In another embodiment, the phosphorus source is a manufactured fertilizer.

Commercially available manufactured phosphate fertilizers are of many types. Some conventional ones are those containing monoammonium phosphate (MAP), triple super phosphate (TSP), diammonium phosphate, ordinary superphosphate and ammonium polyphosphate. All of these fertilizers are produced by chemical processing of insoluble natural rock phosphates in large scale fertilizer-manufacturing facilities. Advantageously, the present invention enables reducing the amount of these fertilizers applied to the plant growth substrate while still maintaining the same amount, or even increasing the amount, of phosphorus uptake from the plant growth substrate.

In another embodiment, the phosphorus source is organic. An organic fertilizer refers to a plant growth substrate amendment derived from natural sources that guarantees, at least, the minimum percentages of nitrogen, phosphate and potash. Examples include plant and animal by-products, rock powders, seaweed, inoculants and conditioners. In a particular embodiment, said organic phosphorus source is from bone meal, meat meal, animal manure, compost, sewage sludge or guano.

Other fertilizers, such as nitrogen sources, may be added to the composition so long as they are not toxic to the *Penicillium* strains of the invention.

The composition of the invention may further comprise one or more biologically active ingredients other than the *Penicillium* strains of the invention. Non-limiting examples of biologically active ingredients include signal molecules such as lipo-chitooligosaccharides (LCO), chitooligosaccharides (CO), chitinous compounds, flavonoids, jasmonic acid or derivatives thereof, linoleic acid or derivatives thereof, linolenic acid or derivatives thereof, or kerrikins; and beneficial microorganisms.

The one or more beneficial microorganisms may have one or more beneficial properties (such as producing a signal molecule, enhancing nutrients and water uptake, promoting and/or enhancing nitrogen fixation, enhancing seed germination, etc.). Examples of beneficial microorganisms include diazotrophs bacteria, such as bacterium from the *Rhizobium* spp., the *Bradyrhizobium* spp., the *Azorhizobium* spp., the *Sinorhizobium* spp., or the *Mesorhizobium* spp. genera; and mycorrhiza such as endomycorrhiza (including endomycorrhiza of the *Glomus* or of the *Gigaspora* genera) or ectomycorrhiza (including ectomycorrhizal of the *Basidiomycota, Ascomycota* or *Zygomycota* phyla).

The compositions of the invention may further comprise at least one inoculum of *Penicillium radicum, Penicillium biliae, Penicillium expansum* and/or *Penicillium spinulosum*.

The compositions of the invention may further comprise one or more micronutrients such as vitamins, carotenoids, macrominerals (e.g. calcium, magnesium, potassium, sodium, iron), trace minerals, organic acids or combinations thereof.

The composition of the invention may further comprise one or more biostimulants. Biostimulants may enhance metabolic or physiological processes such as respiration, photosynthesis, ion uptake or nutrient delivery. Examples of biostimulants include seaweed extracts, humic acids, fulvic acids, myoinositol and glycine.

The composition of the invention may further comprise one or more polymers. Polymers can be used in the agricultural industry for agrochemical delivery, heavy metal removal, water retention and/or water delivery. Examples of polymers include natural polymers such as agar, starch, alginate, pectin or cellulose; synthetic polymers, and biodegradable polymers such as polycaprolactone, polylactide or poly(vinyl alcohol).

The composition of the invention may further comprise one or more wetting agents. Wetting agents are commonly used on soils, particularly on hydrophobic soils, to improve the infiltration and/or penetration of water into a soil. Examples of wetting agents include adjuvants, oils, surfactants, buffers and acidifiers.

The composition of the invention may further comprise one or more surfactants, in particular non-ionic or anionic surfactants. Preferably, the surfactant will cause as little harm to the activity of the strains of the invention as possible, and will enable wetting and emulsifying the plant growth substrate and/or plant. Preferably, the surfactant will have a low phytotoxicity.

Improvement of Plant Growth Conditions

The present inventors showed that *Penicillium brasilianum* was able to solubilize tri-calcium phosphates with at least the same efficiency as the known *Penicillium radicum* mentioned above, as confirmed in the examples below.

The present invention thus concerns the use of an inoculum of at least one strain of *Penicillium brasilianum*, as defined in the section "Inoculum of *Penicillium brasilianum*" above for improving plant growth conditions.

By "improving plant growth conditions" is meant herein that the growth conditions of the plant are improved by the presence of the inoculum of the invention. In particular, the growth conditions are improved by enhancing the availability of phosphorus and/or micronutrients for plant uptake from the plant growth substrate. This improvement of the growth conditions preferably enables enhancing plant growth, increasing the phosphorus uptake of the plant, increasing the foliar or roots biomass and/or increasing the yield of the plant (such as increasing the foliar, roots, fruits and/or grains biomass, and/or increasing leaves, roots, vegetables, fruits and/or grains number).

Accordingly, the present invention also concerns a method of enhancing plant growth, said method comprising applying an effective amount of an inoculum of at least one strain of *Penicillium brasilianum*, as defined in the section "Inoculum of *Penicillium brasilianum*" above, to a plant growth substrate and/or in or on a plant to be grown.

In the context of the invention, the term "enhancing plant growth" means increasing growth rate, increasing plant yield (including increasing foliar, roots, fruits, vegetables and/or grains biomass and/or increasing leaves, roots, vegetables or fruits number), increasing quality of harvest, increasing roots number, increasing root mass, increasing root volume, increasing leaf area, increasing plant stand, increasing plant vigor or combinations thereof.

The present invention also concerns a method of increasing the availability of phosphorus and/or micronutrients for plant uptake from a plant growth substrate, said method comprising applying to the plant growth substrate and/or in or on the plant to be grown, an effective amount of an inoculum of *Penicillium brasilianum* as defined in the section "Inoculum of *Penicillium brasilianum*" above.

By "micronutrients" is meant herein nutrients which are needed for plant growth, plant health and/or plant development, such as copper, ion or zinc.

By "increasing the availability of phosphorus for plant uptake" is meant herein inducing or increasing phosphate solubilization in the plant growth substrate, that is to say inducing or increasing the conversion of insoluble phosphate, such as rock phosphate, into a soluble phosphate form, and/or improving the efficiency of fertilizers.

By "increasing the availability of micronutrients for plant uptake" is meant herein inducing or increasing the conversion of micronutrients fixed to the plant growth substrate into a soluble form.

The present invention further concerns a method for increasing the phosphorus uptake of a plant and/or increasing the foliar or roots biomass and/or increasing the yield (such as increasing the foliar, roots, fruits and/or grains biomass, and/or increasing leaves, roots, vegetables, fruits and/or grains number) of a plant, said method comprising applying an effective amount of an inoculum of at least one strain of *Penicillium brasilianum*, as defined in the section "Inoculum of *Penicillium brasilianum*" to the plant growth substrate in which the plant is grown and/or on or in the plant which is grown.

In a particular embodiment of the methods of the invention, at least one of the strains of *Penicillium brasilianum* described in the section "Inoculum of *Penicillium brasilianum*" above are used, more preferably at least two or all the strains are used.

In the methods of the invention, the step of applying to the plant growth substrate the inoculum of at least one strain of *Penicillium brasilianum*, as defined in the section "Inoculum of *Penicillium brasilianum*" above, preferably comprises applying to the plant growth substrate the composition of the invention. The inoculum or the composition may be applied to the plant growth substrate using methods well-known from the skilled person, such as by in-furrow application, spraying, coating seeds or foliar application. In a preferred embodiment, the inoculum or composition is applied to the plant growth substrate by in-furrow application or by coating seeds. In a most preferred embodiment, the step of applying to the plant growth substrate the inoculum of at least one strain of *Penicillium brasilianum* comprises introducing the inoculum as a seed coating.

In the context of the invention, the term "effective amount" refers to the sufficient amount to obtain the beneficial or desired results mentioned herein. An effective amount can be administered in a single operation or in several administrations.

The skilled person will be able to determine the amount of inoculum to be applied to the plant growth substrate using routine methods. As will be clear to the skilled person, the suitable application rates will vary according to the type of plant growth substrate, the type of plant, the amount of soluble and insoluble phosphate, and a suitable rate can be determined without difficulty by routine trial for each particular case.

In a particular embodiment of the methods of the invention, the step of applying to the plant growth substrate an inoculum of at least one strain of *Penicillium brasilianum* comprises applying the inoculum to the plant growth substrate in an amount of $1\times10^1$ to $1\times10^{12}$, in particular of $1\times10^5$ to $1\times10^{10}$ colony forming units per hectare. In another particular embodiment of the methods of the invention, the step of applying to the plant growth substrate an inoculum of at least one strain of *Penicillium brasilianum* comprises applying the inoculum as a seed coated with $1\times10^1$ to $1\times10^8$, in particular $1\times10^1$ to $1\times10^6$ colony forming units per seed.

In a particular embodiment, the inoculum of at least one strain of *Penicillium brasilianum*, as defined in the section "Inoculum of *Penicillium brasilianum*" may be used with at least one inoculum of *Penicillium radicum*, *Penicillium biliae*, *Penicillium expansum* and/or *Penicillium spinulosum*.

Since the fungus of the invention have the effect of solubilizing phosphates which may already be present in the plant growth substrate (i.e. those which are native to the plant growth substrate) and also those which are added to the plant growth substrate and hence increasing their efficiency, the inoculum of the invention may be applied alone to plant growth substrates which contain native sources of phosphorus or may be applied to any plant growth substrate in conjunction with added sources of phosphorus.

The methods of the invention may thus further comprise a step of contacting the inoculum of *Penicillium brasilianum* with a source of phosphorus. More particularly, the methods of the invention may further comprise a step of adding a source of phosphorus to the plant growth substrate. The step of adding a source of phosphorus may occur before, after or during the step of applying the inoculum. In a particular embodiment, the source of phosphorus may be an ingredient of the composition of the invention comprising said inoculum. The source of phosphorus is typically as described in the section "Composition" above. Preferably, the source of phosphorus is a manufactured fertilizer or is organic.

In the methods of the invention, the step of applying to the plant growth substrate the inoculum of at least one strain of *Penicillium brasilianum*, as defined in the section "Inoculum of *Penicillium brasilianum*" above, can be carried out prior to seed being sown, simultaneously with the seed being sown (for example as a coating of the seed), following the planting of the seed and/or during the growth of the plant.

It is within the general knowledge of the skilled person that a plant has specific needs in phosphorus for its growth at specific stages of its development. As well-known from the skilled person, these needs and development stages vary according to the plant. Accordingly, the skilled person will be able to determine, for each plant, at which stage of its development the inoculum of the invention should be applied to obtain the best effect on plant growth.

Coated Plant Seeds

In the methods of the invention, the step of applying to the plant growth substrate the inoculum of at least one strain of *Penicillium brasilianum* comprises introducing the inoculum as a seed coating.

Accordingly, the present invention also concerns the use of a composition comprising an inoculum of at least one strain of *Penicillium brasilianum*, as defined in the section "Inoculum of *Penicillium brasilianum*" for coating plant seeds.

As used herein, the term "coated" or "coating" means that the inoculum or composition of the invention is applied to the seed. The seeds do not need to be completely covered with the inoculum or composition of the invention, but need only be at least partially covered.

There are several ways of coating seeds with the composition of the invention, ways known to the skilled person and any suitable method may be used.

Seeds may be coated with the composition of the invention in several ways, for example by spraying or dripping. Spray and drip treatment may be conducted by formulating compositions as defined in the section "Composition" above and spraying or dripping the composition onto a seed via a continuous treating system, such as a drum-type of treater. Batch systems, in which a predetermined batch size of seed and composition are delivered into a mixer may also be employed.

In a particular embodiment, seeds may be coated with the composition of the invention by coating the inside wall of a round container with the composition of the invention, adding seeds, then rotating the container to make the seeds contact the wall and the composition. Such a process is known as "container coating". Seeds can also be coated by combining different coating methods, including soaking methods.

The inoculum of the invention may also be formulated and then dried using air drying, freeze drying or fluid bed drying techniques to produce wettable powder. The wettable powder can then be suspended in water, applied to the surface of seeds, for example by one of the techniques described above, and allowed to dry prior to planting. The wettable powder may be used in conjunction with other seed treatments, such as chemical seed treatments, carriers (such as talc, clay, kaolin, silica gel or kaolinite) or polymers (such as methylcellulose or polyvinylpyrrolidone).

Alternatively, the inoculum of the invention may be applied to a suitable plant growth substrate-compatible carrier, as defined in the section "Composition" above, to reach an appropriate final moisture content. The inoculum of the invention may still be mixed with a carrier comprising a mixture of soluble starch and cellulose suspended in water and used to coat plant seeds, using one of the techniques mentioned above. Alternatively, the inoculum may be grown on a carbon source, which can then be dried and sieved, and the resulting particles adhered to seeds by use of a sticky or adhesive material, for example arabic gum.

In a particular embodiment, the composition used to coat seeds comprises additional ingredients as defined in the section "Composition" above. In a preferred embodiment, the composition further comprises a source of phosphorus as defined in the section "Composition" above.

The present invention also concerns a method for coating plant seeds comprising the use of a composition comprising an inoculum of at least one strain of *Penicillium brasilianum*, as defined in the section "Inoculum of *Penicillium brasilianum*" above. In a particular embodiment, said method comprises applying said composition to a plant seed.

The present invention thus also concerns a plant seed having a coating comprising an inoculum of at least one strain of *Penicillium brasilianum*, as defined in the section "Inoculum of *Penicillium brasilianum*" above.

In a particular embodiment, the coated seed comprises 10 to $1\times10^8$, more preferably $1\times10^1$ to $1\times10^6$ colony forming units of at least one strain of *Penicillium brasilianum*.

The coated plant seed of the invention is particularly useful in the methods of the invention. It can be typically used in those methods for applying the inoculum of the invention.

The present invention will be further illustrated by the figures and example below.

BRIEF DESCRIPTION OF THE DRAWINGS

FIG. 1: pH obtained with the following strains: *Penicillium brevicompactum* O853, *Trichoderma* sp. T41, *Trichoderma* sp. T42, *Trichoderma hamatum* Th3, *Trichoderma* sp. T43, *Trichoderma atroviride* Ta1, *Trichoderma atroviride* Ta2, *Penicillium brasilianum* O64, *Trichoderma* sp. T44, *Penicillium griseofulvum/dipodomyicola* O851, *Penicillium brasilianum* O849, *Penicillium brasilianum* O65, *Trichoderma koningiopsis* O153, *Trichoderma koningiopsis* O81, *Trichoderma koningiopsis* O103, *Penicillium expansum* O854, *Penicillium radicum* O238, *Talaromyces purpurogenus/flavus* O850, *Talaromyces purpurogenus/flavus* O848, *Penicillium cordubense/polonicum* O852, and no strain.

FIG. 2: pH obtained with the following strains: *Trichoderma* sp. T21, *Trichoderma* sp. T22, *Trichoderma* sp. T23, *Trichoderma* sp. T24, *Trichoderma* sp. T25, *Trichoderma* sp. T26, *Trichoderma* sp. T27, *Trichoderma* sp. T28, *Trichoderma* sp. T29, *Trichoderma* sp. T30, *Trichoderma* sp. T31, *Trichoderma* sp. T32, *Trichoderma* sp. T33, *Trichoderma* sp. T34, *Trichoderma hamatum* Th1, *Trichoderma* sp. T35, *Trichoderma hamatum* Th2, *Trichoderma* sp. T36, *Trichoderma* sp. T37, *Trichoderma* sp. T38, *Trichoderma* sp. T39, *Trichoderma* sp. T40, *Penicillium brevicompactum* O853, and no strain.

FIG. 3: pH obtained with the following strains: *Trichoderma* sp. T1, *Trichoderma* sp. T2, *Trichoderma* sp. T3, *Trichoderma* sp. T4, *Trichoderma* sp. T5, *Trichoderma* sp. T6, *Trichoderma* sp. T7, *Trichoderma* sp. T8, *Trichoderma* sp. T9, *Trichoderma* sp. T10, *Trichoderma* sp. T11, *Trichoderma* sp. T12, *Trichoderma* sp. T13, *Trichoderma* sp. T14, *Trichoderma* sp. T15, *Trichoderma* sp. T16, *Trichoderma* sp. T17, *Trichoderma* sp. T18, *Trichoderma* sp. T19, *Trichoderma* sp. T20, *Penicillium brevicompactum* O853, and no strain.

EXAMPLES

Example 1

Figure 1:
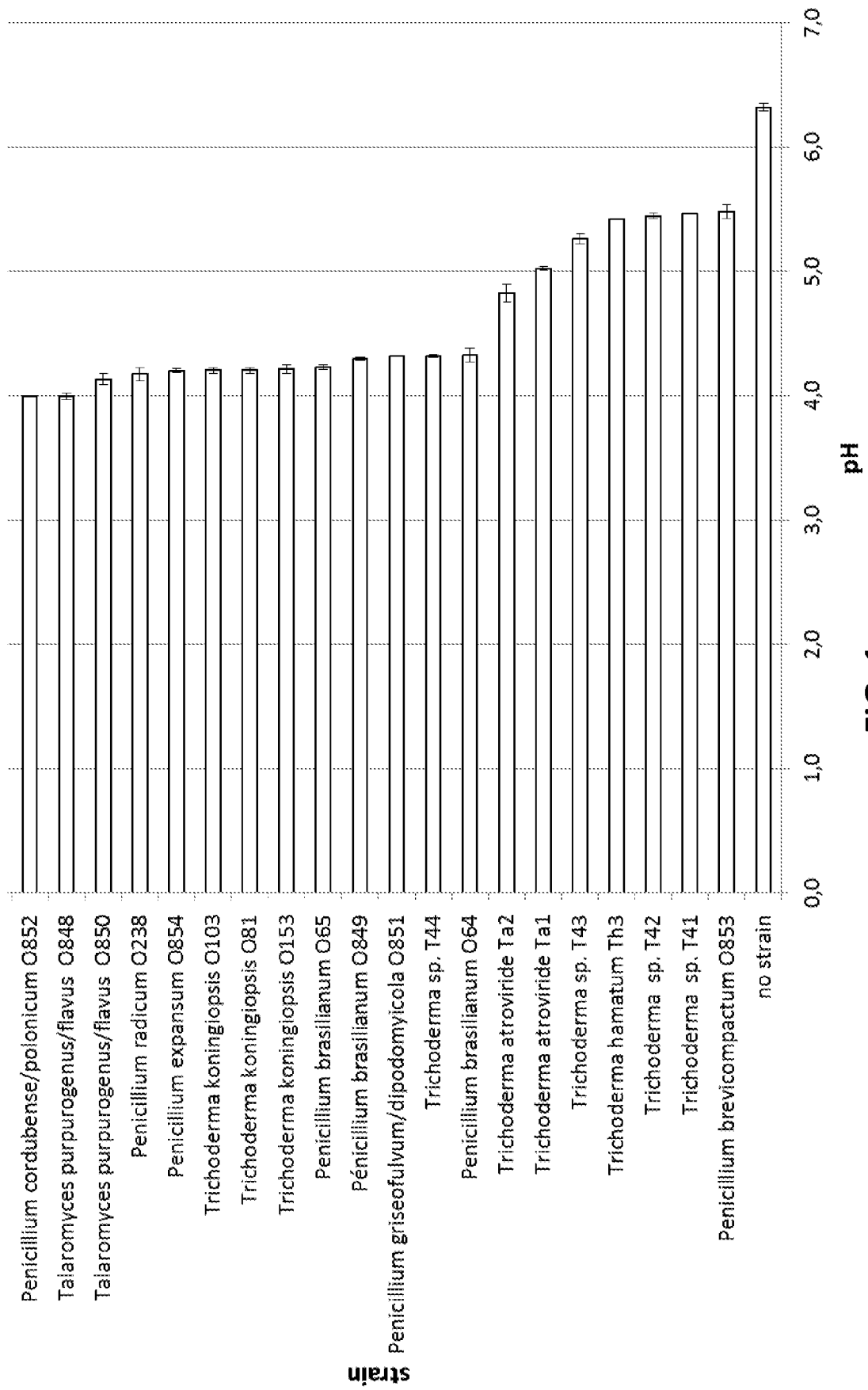
FIGS. 1-3 show histograms displaying the pH level of the medium supernatant in the phosphate solubilization assay of the example with the 62 tested fungi strains.

This example shows that *Penicillium brasilianum* strains are capable of solubilizing phosphorus and are therefore useful to increase availability of phosphorus for plant uptake.

Material and Methods
Biological Material

The screening was performed on 62 strains which were of the *Penicillium* or *Trichoderma* morphotype including:
- *Penicillium radicum* CBS 100489 used as positive control,
- *Penicillium expansum* used as positive control,
- *Penicillium brasilianum* strains O64, O65 and O849,
- one *Penicillium brevicompactum* strain,
- one strain which was identified as belonging either to the species *Penicillium cordubense* or to the species *Penicillium polonicum* (designated as *Penicillium cordubense/polonicum* below),
- one strain which was identified as belonging either to the species *Penicillium griseofulum* or to the species *Penicillium dipodomyicola* (designated as *Penicillium griseofulum/dipomyicola* below),
- two strains which were identified as belonging either to the species *Talaromyces* (sexual state of *Penicillium*) *purpurogenus* or to the species *Talaromyces flavus* (designated as *Talaromyces purpurogenus/flavus* below), and
- 52 *Trichoderma* strains.

Culture Media

Two culture media were used in the present study:
- PDA AES (AEB 152052): potato infusion (5 g/l), dextrose (20 g/l), agar (17 g/l). This medium was used for pre-cultures of strains, viability assays and CFU counting.
- NBRIP-BPB (National Botanical Research Institute's phosphate+colored pH indicator Bromophenol Blue BPB): glucose (10 g/l), $Ca_3PO_4$ (5 g/l), $MgCl_2$ (5 g/l), $MgSO_4$ (2.5 g/), KCl (0.2 g/l), $(NH_4)_2SO_4$ (0.1 g/l), BPB (0.025 g/l), adjusted to a pH 7.0.

"NBRIP-BPB, $OD_{600\ nm}$ Decrease" Assay

This protocol is adapted from the protocol described in Mehta et al. (2001) *Current Microbiology* 43:51-56.

The spores of the tested strains were used either from stocks stored at −80° C. in 12.5% glycerol with a minimal concentration of spores of $3\times10^7$ spores/ml or from precultures obtained as followed.

The strains were cultured in PDA medium at 25° C. and 90% humidity in Petri dishes until obtaining a good level of sporulation (conventionally 7 to 14 days for the strains screened herein). Water with 0.2% Tween was added to each Petri dish and the surface of the dish was gently scratched in order to detach spores. The spore suspension was recovered and filtered through a 40-100 µm filter in order to remove mycelium debris. The number of spores was counted in order to known the spore concentration.

The spores were used to inoculate NBRIP-BPB medium in a flask at a final concentration of $1\times10^6$ spores/ml. Simultaneously, a small amount of spores was inoculated in PDA medium in order to confirm the satisfactory growth of the strains.

The flasks were cultured at 25° C. under an agitation of 180 rpm during 6 days.

A sample of each flask was collected and clarified by centrifugation at 8000 rpm during 20 min. The culture supernatants were recovered and studied by spectrophotometry: the optical density at 600 nm ($OD_{600\ nm}$) was measured in triplicates. The OD values were analyzed by ANOVA and the results of the analysis were displayed in the form of dot plots, since the strain was identified, by the ANOVA analysis, as being the most important variability factor.

"pH-pH Decrease" Assay

The pH of the medium supernatant obtained above was measured.

Results

The inventors isolated several hundreds of new fungic strains from different sources (wheat dead plant tissue from Bresse in France or wheat plant surface from Bourgogne in France). Among these new strains, they screened 62 strains of the *Penicillium* or *Trichoderma* morphotype in order to identify new strains capable of acidifying the culture medium by secreting organic acids and thereby capable of solubilizing phosphorus from soil.

This screening was performed using two methods, one adapted from the method disclosed in Mehta et al. (2001) *Current Microbiology* 43:51-56 and the other consisting in measuring the final pH of the culture supernatants compared to a non-inoculated control.

Two strains were used as a positive control: the *Penicillium radicum* strain CBS 100489 disclosed in Whitelaw et al. (1999) *Soil Biology Biochem* 31:655-665 and the *Penicillium expansum* strain.

Figure 2:
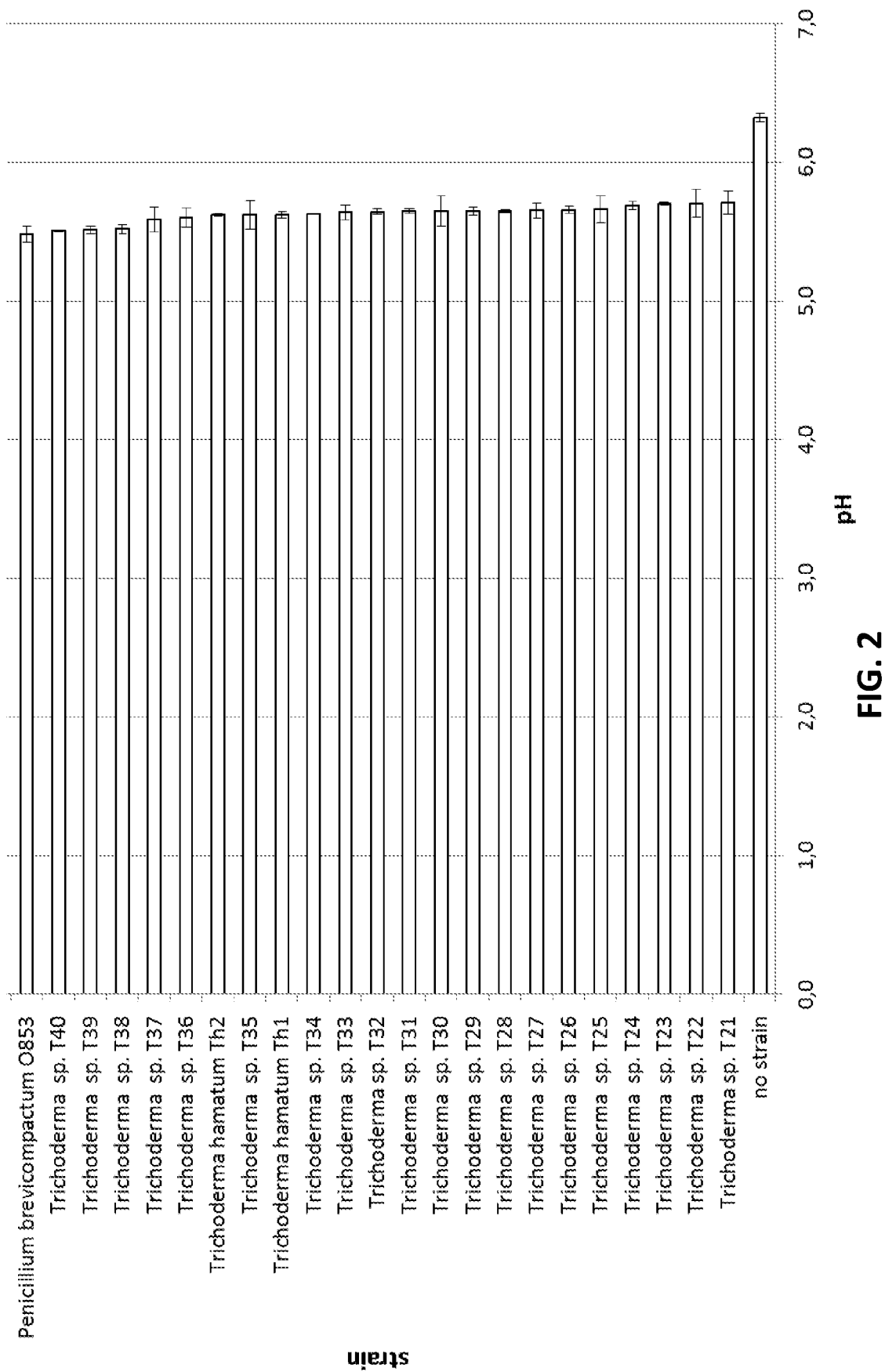
Figure 3:
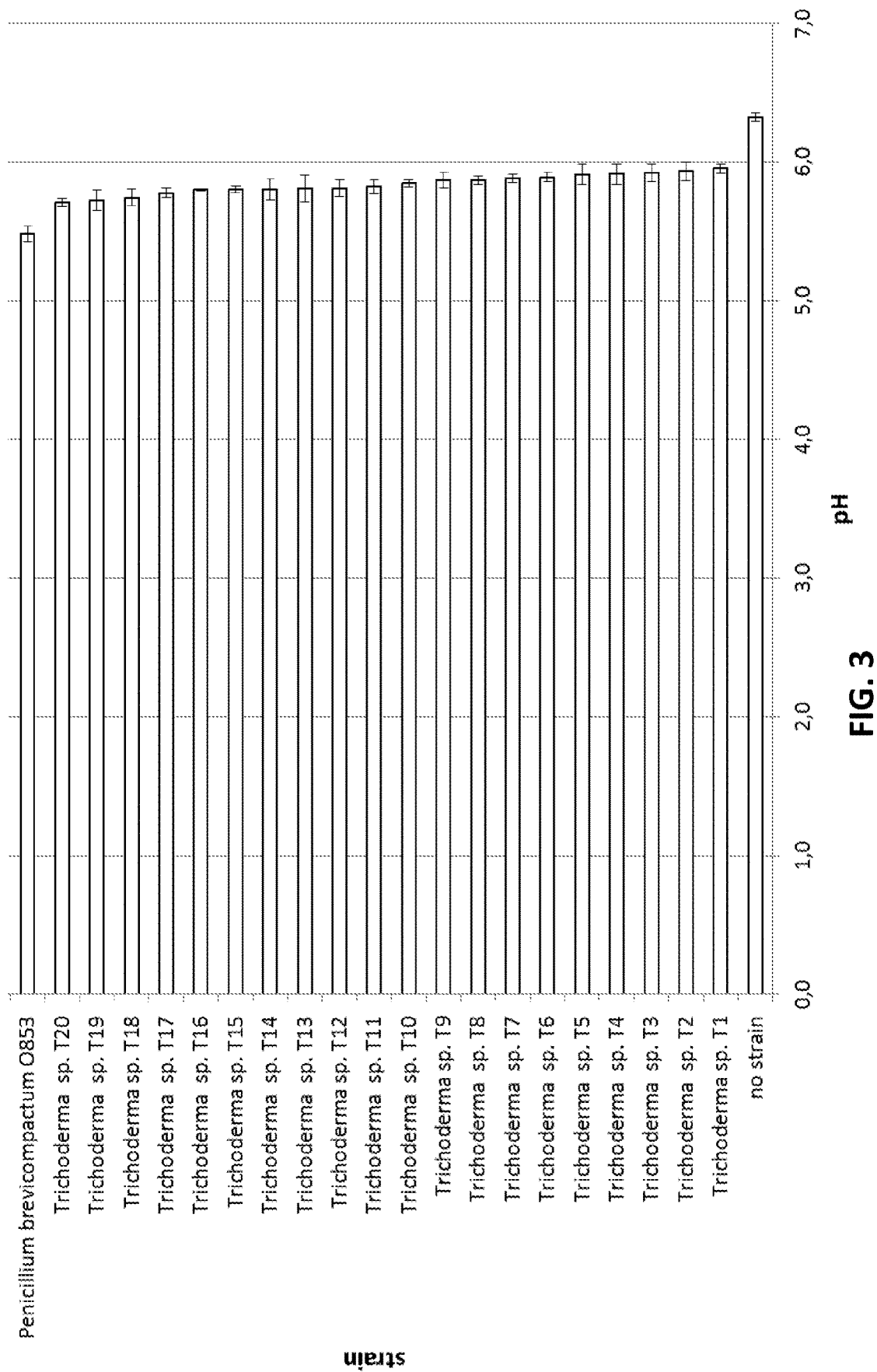

The results of the assay "pH, pH decrease", displayed on FIGS. 1-3, show that, among the 62 tested strains, only three strains show a pH decrease higher than the positive control strain *Penicillium radicum* and of the *Penicillium expansum* strain. It is the case of the *Penicillium cordubense/polonicum* O852 and of the *Talaromyces* (sexual state of *Penicillium*) *purpurogenus/flavus* strains O848 and O850. However, since *P. polonicum* and *T. purpurogenus/flavus* are pathogenic species, the inventors considered that they were not the best candidate suitable for plants or soil application, which display a higher pH decrease than the positive control strains.

However, a limited number of other strains showed a decrease of pH similar to that obtained with the *Penicillium radicum* strain. It is the case of the *Penicillium brasilianum* strains O64, O65 and O849, of the *Penicillium griseofulvum/dipodomyicola* strain O851 (which is known as producing a dangerous mycotoxin and is thus not suitable for plants or soil application), and of the *Trichoderma koningiopsis* strains O81, O103 and O153 (which are strains from a *Trichoderma* species known to solubilize phosphorus as confirmed by Barrera et al (2014) Poster "Strains of *Trichoderma* sp. and their Capacity to Mobilise Phosphorus"), which are thus also usable as biofertilizers.

All the other tested strains, including strains from other *Penicillium* species than *Penicillium brasilianum*, such as *Penicillium brevicompactum*, have a very weak pH decrease compared to the positive control, and are thus not capable to solubilize phosphorus efficiently.

Figure 4:
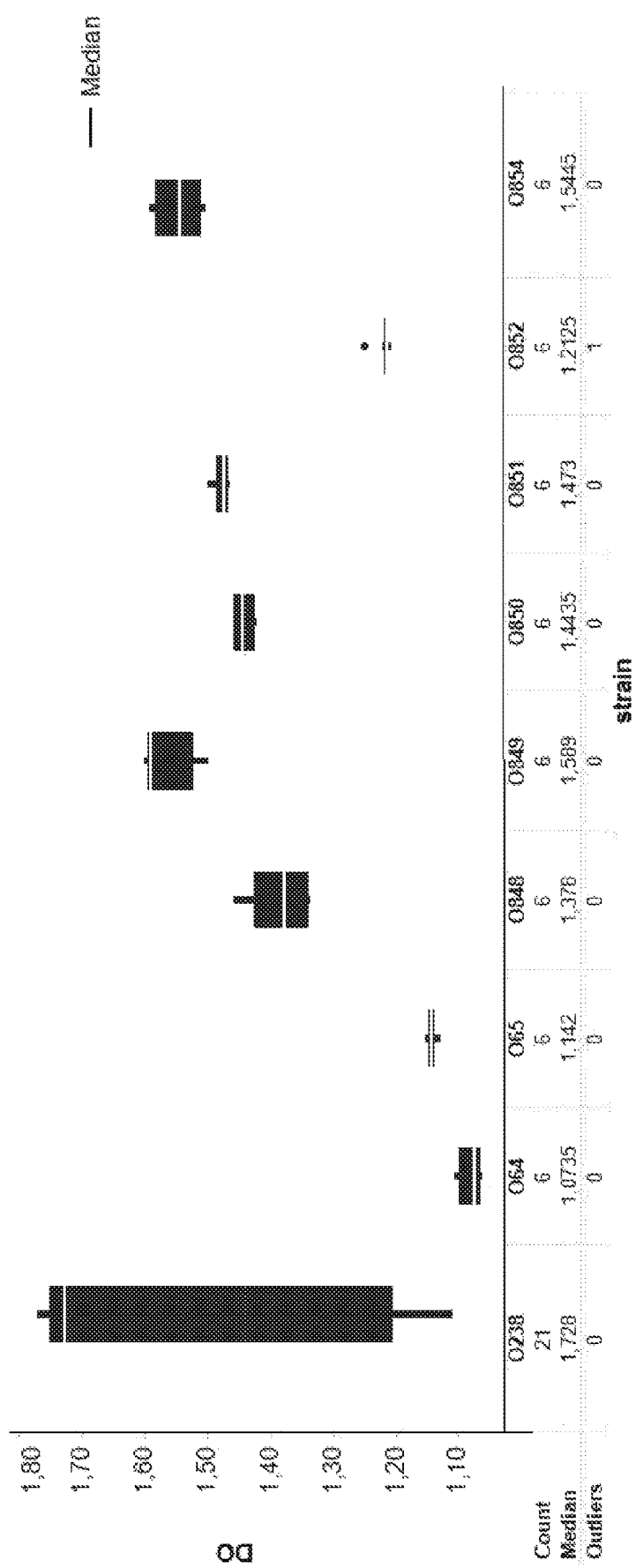
FIG. 4 shows box plots displaying the $OD_{600\,nm}$ value of the medium supernatant in the phosphate solubilization assay of the example with the tested *Penicillium* strains. Box plots obtained with the following strains: *Penicillium radicum* O238, *Penicillium brasilianum* O64, *Penicillium brasilianum* O65, *Talaromyces purpurogenus/flavus* O848, *Penicillium brasilianum* O849, *Talaromyces purpurogenus/flavus* O850, *Penicillium griseofulvum/dipodomyicola* O851, *Penicillium cordubense/polonicum* O852 and *Penicillium expansum* O854.

The results of the assay "NBRIP-BPB, $OD_{600\ nm}$ decrease" and of the ANOVA analysis, displayed in Table 1 below and on FIGS. 4-5, show a great diversity in the capacity of the tested strains to secrete organic acids and emphasize the fact that *Penicillium brasilianum* species are at least as efficient (or even more efficient) in solubilizing phosphorus as the positive controls.

TABLE 1

Results of the ANOVA analysis

| Y(num.) | X(cat.) | p-value | FStat | S2Btwn | S2Wthn | dfBtwn | dfWthn | n |
|---|---|---|---|---|---|---|---|---|
| DO | strain | 3.11E−51 | 137.179453 | 34.119223 | 2.03497881 | 11 | 90 | 102 |
| DO | role | 2.47E−15 | 48.1537594 | 17.8278926 | 18.3263092 | 2 | 99 | 102 |
| DO | series | 3.73E−03 | 3.48200725 | 6.51757562 | 29.6366262 | 6 | 95 | 102 |
| DO | date | 3.73E−03 | 3.48200725 | 6.51757562 | 29.6366262 | 6 | 95 | 102 |

Indeed, the *Penicillium brasilianum* strains O64 and O65 and the *Penicillium cordubense/polonicum* strain O852 show a decrease of $OD_{600\ nm}$ stronger than the positive control strains *Penicillium radicum* and *Penicillium expansum*.

Additionally, the *Penicillium brasilianum* strain O849 shows a decrease of $OD_{600\ nm}$ similar to that obtained with the *Penicillium radicum* strain, while the other tested strains, including strains from other *Penicillium* species than *Penicillium brasilianum*, such as *Penicillium brevicompactum*, have a decrease of $OD_{600\ nm}$ weaker than the positive control, and are thus not capable to solubilize phosphorus efficiently in the present experimental conditions.

Accordingly, in this example, the inventors identified one *Penicillium* species which is particularly interesting for use for solubilizing phosphorous in the soil.

This is the case of *Penicillium brasilianum* for which all the tested strains showed a better or similar capacity to solubilize phosphorus than the known *Penicillium radicum* strain.

It should be noted that not all *Penicillium* species have such capacities since some *Penicillium* species such as *Penicillium brevicompactum* was unable to solubilize phosphorus in the present experimental conditions.

Example 2

This example shows that *Penicillium brasilianum* strains are capable of improving exportation of phosphorus from the soil to the foliar parts of ray-grass in culture.
Materials and Methods
Biological Material
The assay was performed with 4 strains which were of the *Penicillium* and *Trichoderma* morphotype including:
*Penicillium radicum* CBS 100489 used as positive control (O238), and
*Penicillium brasilianum* strains O64, O65 and O849.
The plant used for the assay is ray-grass (*Lolium perenne*), more particularly English ray-grass (Maisons des Gazons, mixture of 3 varieties: 30% Amadeus/40% Greenway/30% Advent).
Tested Conditions
7 different conditions were tested:
Non inoculated deficient dirt as control,
Dirt with tricalcium phosphate at a dose equivalent to 100 ppm of $P_2O_5$, as negative control,
Dirt with tricalcium phosphate at a dose equivalent to 100 ppm of $P_2O_5$, inoculated with *Penicillium radicum* CBS 100489 (O238) at $10^5$ cfu/g of dry dirt, as positive control,
Dirt with tricalcium phosphate at a dose equivalent to 100 ppm of $P_2O_5$, inoculated with *Penicillium brasilianum* strain O64 at $10^5$ cfu/g of dry dirt,
Dirt with tricalcium phosphate at a dose equivalent to 100 ppm of $P_2O_5$, inoculated with *Penicillium brasilianum* strain O65 at $10^5$ cfu/g of dry dirt,
Dirt with tricalcium phosphate at a dose equivalent to 100 ppm of $P_2O_5$, inoculated with *Penicillium brasilianum* strain O849 at $10^5$ cfu/g of dry dirt,
Dirt with monocalcium phosphate at a dose equivalent to 100 ppm of $P_2O_5$, as positive control.
Experimental Device
A specific container was used for the assay. This container comprises 3 parts which enable:
Controlling independently the germination conditions,
Keeping humidity and aeration of the substrate at levels which are favorable for plants germination and growth,
Assaying products in mixture with several types of support (sand, dirt . . . ).
The pots comprise 3 overlapped boxes:
A box without any bottom (upper part) where the seedling is carried out on 300 g of sand, at 800 mg of ray-grass by pot;
A box with a perforated bottom (intermediate part) enabling strands of tissues with a sufficient capillarity to keep the compartment at the desired humidity to pass through. This bow comprises 300 g of medium (dirt+ product to be tested);
A box with a bottom (lower part) in which water or nutritive solution is provided.
Efficacy of fungus strains to improve bioavailability of phosphorus for the plant is determined by comparing the bioavailability of phosphorus of a natural phosphate (tricalcium phosphate or phytate) with or without fungus in the medium.
A mineral highly soluble phosphate fertilizer, namely pure monocalcic phosphate, was added to the assay condition "Dirt+mineral P" and phytases were added to the pot (10-40 U/pot) for the assay condition "Dirt+organic P" in order to validate the system.
A contact period of 2 weeks between the substrate and the phosphate products was observed. It enables solubilization of phosphorus of the product and its integration in the pool of available phosphorus. After two weeks of contact, the upper pots, which comprise 10-day seedlings, are transferred on the intermediate pots.
A mineral fertilization deficient in phosphorus was brought to each pot of each condition test. It provides to ray-grass non-limitative amounts of N, $K_2O$, MgO, CaO and oligo elements.
The assays were performed in controlled conditions with a "day" temperature of 25° C. and a "night" temperature of 19° C. The photoperiod was constituted of 16 hours of lighting and 8 hours of darkness. Humidity of the substrate was kept at 100% of its retention capacity. 3 independent tests were conducted with 3 repetitions for each condition tested.
Measurements
One cut of ray-grass was performed 12 weeks after seedling.
The phosphorus content of the dry biomass was determined after drying at 75° C. These values enable calculating the amount of phosphorus exported to the upper parts of the plant, for each pot of the assay.

—Foliar Biomass (WEIDRY):

The measurement of the foliar biomass by pot (dry matter) provides information on plant matter production according to the different tested doses compared to the control "Dirt" and the control "Dirt+tricalcium P".

—Phosphorus Content in the Upper Parts of the Plant (CONP):

Quantification of the phosphorus content in the upper parts of ray-grass provides information on the availability of phosphorus of the experimental system according to the different tested doses compared to the control "Dirt" and the control "Dirt+tricalcium P".

—Exported Foliar Phosphorus (PEXPORT):

Calculation of phosphorus exported from the experimental system to the upper parts of ray-grass enables comparing the different tested strains globally compared to the control "Dirt" and the control "Dirt+tricalcium P".

PEXPORT=WEIDRY×CONP

Statistical Analysis

All the data were interpreted by ANOVA.

ANOVA validation is based on data homogeneity and the respect of the Normal law, in other words the repartition of the data according to a Gauss curve.

To check these hypotheses, different tests were used:
The Skewness test enables measuring the curve symmetry.
The Kurtosis test enables determining the curve kurtosis.
The Barlett test enables checking the equality of the standard deviations between products.

The results of the treatments are indicated by a letter in the results tables. Treatments without any letter in common are considered as significatively different with a confidence level of 95%.

Results

Behavior of the Controls

The phosphorus source ($P_2O_5$) of the assay was validated by the coherent behaviors of the positive and negative controls.

Compared to the control "Dirt", monocalcium phosphate is assimilable by the plants, whereas tricalcium phosphate is not assimilable.

Thus, the provision of tricalcium phosphate does not significantly modify the growth and nutrition in phosphorus of the plants, whereas the positive control monocalcium phosphate shows a significant exportation of phosphorus to the upper parts.

TABLE 2

Foliar biomass (WEIDRY). phosphorus content (CONP) and exported phosphorus (PEXPORT) of the negative and positive controls at 12 weeks (cut 3) after seedling.

| Treatment name | Rating Type | | |
|---|---|---|---|
| | WEIDRY | CONP | PEXPORT |
| | Rating Unit | | |
| | g | % | mg |
| | Sample Size. Unit | | |
| | 1 plot | 1 plot | 1 plot |
| | Description | | |
| | CUT 3 | CUT 3 | CUT 3 |
| DIRT | 1.254 a | 1.014 a | 1.262 a |
| | (100.00%) | (100.00%) | (100.00%) |

TABLE 2-continued

Foliar biomass (WEIDRY). phosphorus content (CONP) and exported phosphorus (PEXPORT) of the negative and positive controls at 12 weeks (cut 3) after seedling.

| Treatment name | Rating Type | | |
|---|---|---|---|
| | WEIDRY | CONP | PEXPORT |
| | Rating Unit | | |
| | g | % | mg |
| | Sample Size. Unit | | |
| | 1 plot | 1 plot | 1 plot |
| | Description | | |
| | CUT 3 | CUT 3 | CUT 3 |
| DIRT + tricalcium P | 1.174 a | 1.066 a | 1.234 a |
| | (93.62%) | (105.04%) | (97.76%) |
| DIRT + monocalcium P | 1.776 b | 1.401 b | 2.462 b |
| | (141.58%) | (138.12%) | (195.12%) |

Means followed by same letter or symbol do not significantly differ (P = .05. Dunnett's vs. Control)

Mean comparisons performed only when AOV Treatment P(F) is significant at mean comparison OSL In view of the results of the analysis of the controls, the assay for identifying fungus strains enabling improving assimilation of soil phosphorus is coherent concerning the phosphorus source used.

Selectivity

No symptom of cytotoxicity was detected on the culture during the assay. No notable visual effect was observed on foliar biomass between the different treatments.

Results of the Cut 3 Months after Seedling

As shown in Table 3, as expected, the results of the positive control "Dirt+monocalcium phosphorus" show a statistically significant increase of phosphorus at the foliar level after 3 months of culture.

None of the fungus strain has a statistically significant effect on the phosphorus exportation in the present experimental conditions compared to the positive control "Dirt+monocalcium phosphorus". However, it can be observed from Table 3 that the *Penicillium brasilianum* strain O849 shows a notable improvement of 9-10% in phosphorus exportation compared to the control "Dirt+tricalcium phosphorus", 3 months after seedling.

Accordingly, in the present experimental conditions, this strain has a long term effect, mainly targeting foliar biomass increase.

Furthermore, the *Penicillium brasilianum* strain O65 showed an improvement of about 4% in phosphorus exportation compared to the control "Dirt+tricalcium phosphorus", after 3 months of culture, improvement which is similar to the one observed with the positive control *Penicillium radicum* CBS 100489.

Finally, the *Penicillium brasilianum* strain O64 induced a 2% increase in foliar biomass, after 3 months of culture, compared to the control " "Dirt+tricalcium phosphorus.

TABLE 3

Foliar biomass (WEIDRY), phosphorus content (CONP) and exported phosphorus (PEXPORT) 12 weeks after seedling.

| | Rating Type | | | | | |
|---|---|---|---|---|---|---|
| | WEIDRY | WEIDRY | CONP | CONP | PEXPORT | PEXPORT |
| | Rating Unit | | | | | |
| | g | g | % | % | mg | mg |
| | Sample Size, Unit | | | | | |
| | 1 plot | 1 plot | 1 plot | 1 plot | 1 plot | 1 plot |
| | Description | | | | | |
| Treatment Name | CUT 3 | CUT 3 | CUT 3 | CUT 3 | CUT 3 | CUT 3 |
| DIRT | 1.254 (100.00%) | 1.254 | 1.014 (100.00%) | 1.014 | 1.262 (100.00%) | 1.262 |
| DIRT + tricalcium P | 1.174 b (100.00%) | 1.174 a | 1.066 b (100.00%) | 1.066 a | 1.234 b (100.00%) | 1.234 a |
| DIRT + tricalcium P + 0238 10E5 | 1.227 b (104.52%) | 1.227 a | 1.051 b (98.64%) | 1.051 a | 1.274 b (103.25%) | 1.274 a |
| DIRT + tricalcium P + 0849 10E5 | 1.308 b (111.37%) | 1.308 a | 1.038 b (97.39%) | 1.038 a | 1.357 b (109.98%) | 1.357 a |
| DIRT + tricalcium P + 064 10E5 | 1.195 b (101.75%) | 1.195a | 1.028 b (96.45%) | 1.028 a | 1.223 b (99.16%) | 1.223 a |
| DIRT + tricalcium P + 065 10E5 | 1.234 b (105.07%) | 1.234 a | 1.051 b (98.64%) | 1.051 a | 1.282 b (103.91%) | 1.282 a |
| DIRT + monocalcium P | 1.776 a (151.23%) | 1.776 | 1.401 a (131.49%) | 1.401 | 2.462 a (199.59%) | 2.462 |

Means followed by same letter or symbol do not significantly differ (P = .05, Student-Newman-Keuls) Mean comparisons performed only when AOV Treatment P(F) is significant at mean comparison OSL.

In conclusion, the inventors demonstrated that, in a specific experimental design, the *Penicillium brasilianum* strains O849 and O65 had the specific advantage of improving phosphorus exportation in the upper parts of the plant, in particular of ray-grass, of respectively about 10 and about 4%, after 3 months of culture, while the *Penicillium radicum* strain CBS 100489, known to solubilize phosphate, only induced an about 3% improvement.

The invention claimed is:

1. A method comprising improving plant growth conditions by applying an effective amount of an inoculum of at least one strain of *Penicillium brasilianum* (i) to the plant growth substrate, (ii) in the plant to be grown, (iii) on the plant to be grown, or any combination of (i), (ii) and (iii), wherein the at least one strain of *Penicillium brasilianum* is selected from the group consisting of the *Penicillium brasilianum* strain 064 deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54519, the *Penicillium brasilianum* strain 065 deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54520, and the *Penicillium brasilianum* strain 0849 deposited under the Budapest Treaty with the Centralbureau voor Schimmelcultures (CBS, Uppsalalaan 8, 3584 CT Utrecht, Netherlands) on 27 Oct. 2016 under Accession number CBS 141988, and mixtures thereof.

2. The method according to claim 1, wherein the inoculum is a mixture of at least two strains of *Penicillium brasilianum*.

3. The method according to claim 1, wherein the inoculum is used in combination with at least one inoculum of *Penicillium radicum, Penicillium biliae, Penicillium expansum*, and *Penicillium spinulosum*.

4. A method comprising enhancing plant growth by applying an effective amount of an inoculum of at least one strain of *Penicillium brasilianum* (i) to the plant growth substrate, (ii) in the plant to be grown, (iii) on the plant to be grown, or any combination of (i), (ii) and (iii), wherein the at least one strain of *Penicillium brasilianum* is selected from the group consisting of the *Penicillium brasilianum* strain 064 deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54519, the *Penicillium brasilianum* strain 065 deposited under the Budapest Treaty with the Mycothèque de l'Université Catholique de Louvain (MUCL, Belgian Coordinated Collections of Microorganisms, Université catholique de Louvain, Croix du Sud 2, 1348 Louvain-la-Neuve, Belgium) on 11 Jul. 2013 under Accession number MUCL 54520, and the *Penicillium brasilianum* strain 0849 deposited under the Budapest Treaty with the Centralbureau voor Schimmelcultures (CBS, Uppsalalaan 8, 3584 CT Utrecht, Netherlands) on 27 Oct. 2016 under Accession number CBS 141988, and mixtures thereof.

5. The method according to claim 4, wherein said applying to the plant growth substrate the inoculum of at least one strain of *Penicillium brasilianum* comprises introducing the inoculum as a seed coating.

6. The method according to claim 4, further comprising adding a source of phosphorus to the plant growth substrate.

7. The method according to claim 4, wherein the plant is a crop plant.

8. The method according to claim 7, wherein the plant is a cereal.

* * * * *